United States Patent
Uomoto et al.

[11] Patent Number: 5,380,745
[45] Date of Patent: Jan. 10, 1995

[54] MEDICINAL COMPOSITION

[75] Inventors: Katsuhito Uomoto; Tomoko Shomura; Mitsuyo Matsumoto; Masayuki Takagi; Takao Shimizu; Susumu Kiriya, all of Kanagawa, Japan

[73] Assignee: Meiiji Seika Kaisha, Ltd., Tokyo, Japan

[21] Appl. No.: 113,358

[22] Filed: Aug. 30, 1993

Related U.S. Application Data

[63] Continuation of Ser. No. 846,076, Mar. 5, 1992, abandoned.

[30] Foreign Application Priority Data

Mar. 8, 1991 [JP] Japan .................................. 3-043461

[51] Int. Cl.$^6$ ............................................. A61K 31/40
[52] U.S. Cl. .................................................... 514/410
[58] Field of Search .......................................... 514/410

[56] References Cited

FOREIGN PATENT DOCUMENTS 0179583 4/1986 European Pat. Off. ...... A61K 47/00
0382173 8/1990 European Pat. Off. ... C07D 273/00

*Primary Examiner*—Marianne M. Cintins
*Assistant Examiner*—K. Weddington
*Attorney, Agent, or Firm*—Sughrue, Mion, Zinn, Macpeak & Seas

[57] ABSTRACT

A medicinal composition comprising a practically water-insoluble anthelmintic compound such as PF1022 substance, which is a cyclic depsipeptide compound, as an active ingredient, and one or more compounds selected from either or both of nonionic surfactants and fats and oils, optionally together with one or more aqueous solvents, wherein the total content of the additives is adjusted to not less than 1 part by weight, preferably from 5 to 50 parts by weight, based on the anthelmintic compound. This composition makes it possible to elevate water-solubility of the anthelmintic comopund and thus enhance its anthelmintic effect.

11 Claims, No Drawings

MEDICINAL COMPOSITION

This is a continuation of application Ser. No. 07/846,076 filed Mar. 5, 1992, now abandoned.

FIELD OF THE INVENTION

This invention relates to a medicinal composition containing known practically water-insoluble anthelmintic PF1022 substance or practically water-insoluble analogues thereto as an active ingredient, wherein the water-solubility of the compound is improved and the anthelmintic effect of the compound when administered to take effect at digestive tract is enhanced.

BACKGROUND OF THE INVENTION

Known techniques for producing medicinal preparations containing practically water-insoluble drugs effective at digestive tract, which are employed in order to elevate water-solubility of the drugs and to promote absorption of the drugs via the digestive tract, include conversion into an amorphous form, inclusion within cyclodextrin, dissolution in organic solvents and dry- or wet-powdering.

EP-A-179583 (JP-A-61-91117) discloses a composition containing a practically water-insoluble drug, surfactant and a fat-soluble compound such as vitamin K or propylene glycol.

PF1022 Substance is a known cyclic depsipeptide compound represented by the formula (cf. EP-A-382173).

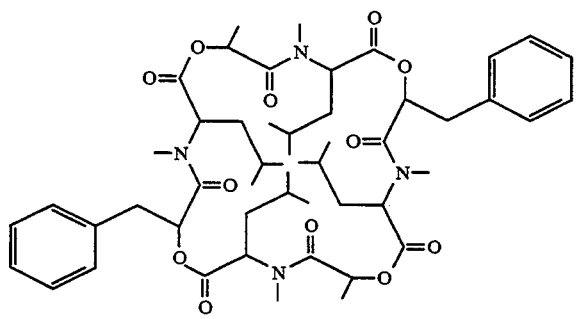

This compound is one of the anthelmintic compounds which can be obtained, in accordance with the method described in EP-A-382173, from a culture of a microorganism isolated from a plant sample, which has been deposited with the Fermentation Research Institute, Agency of Industrial Science and Technology, Japan since Jan. 24, 1989 under the deposit number FERM BP-2671 in accordance with the Budapest Treaty.

PF1022 Substance exerts an anthelmintic effect on parasitic infection in digestive tracts of human, livestock, poultry, experimental animals, and companion animals, such as swine, horse, cattle, rabbit, sheep, goat, fowl, duck, turkey, rat, mouse, guinea pig, monkey, dog, cat, a small bird. PF1022 Substance, when used alone, shows a particularly marked anthelmintic effect on parasites in digestive tract of unigastric animals such as fowl, dog, cat and swine. In the case of rumenal animals such as cattle, sheep and goat, however, it is required to administer 5 to 10 times as much dosage as in the case of unigastric animals. This might be because PF1022 substance cannot attain a concentration or time enough to exert its efficacy in the infected sites in these rumenal animals, since it has an extremely poor solubility in water and therefore is hardly dissolved and dispersed in the digestive tract. Accordingly it is considered that the frequency and time of the contact of PF1022 substance with parasites can be increased by elevating its solubility in water and, as a result, the anthelmintic effect can be enhanced thereby.

SUMMARY OF THE INVENTION

An object of the present invention is to provide a medicinal composition containing PF1022 substance or an analogue thereto as an active ingredient, wherein the solubility of PF1022 substance or an analogue thereto in water is elevated and the anthelmintic effect of PF1022 substance or an analogue thereto is enhanced when administered to take effect at digestive tract.

Anthelmintics exert their effect when a certain amount of the drugs come into contact with parasites or are absorbed by parasites. It seems that the frequency and time of the contact of the drugs with parasites would vary depending on the environment of the infected sites of the host (a factor relating to the parasites) and the properties of the drug (a factor relating to the drug). PF1022 Substance is practically insoluble or hardly dispersible in water. It is considered that poor in vivo dispersion and dissolution of PF1022 substance is mainly attributed to its poor solubility and dispersibility and, therefore, an attempt to improve the properties of PF1022 substance was made. As a result, it was found that solubility and dispersibility of PF1022 substance can be improved by formulating it into a medicinal composition together with specifically selected additive(s). Further, the resulting medicinal composition shows an enhanced anthelmintic effect of PF1022 substance not only on rumenal animals but also on unigastric animals.

DETAILED DESCRIPTION OF THE INVENTION

The term "practically (substantially) water-insoluble analogues" includes cyclic depsipeptide compounds.

Available as the additives to be used in the medicinal composition of the present invention are nonionic surfactants, fats and oils, aqueous solvents such as polyhydric alcohols and oil absorbing carriers. More specifically, one or more compounds selected from either or both of nonionic surfactants and fats and oils are preferably used. Examples of the nonionic surfactants include glycerol fatty acid esters, sorbitan fatty acid esters, polyoxyethylene sorbitan fatty acid esters, polyoxyethylene glycerol fatty acid esters, polyoxyethylene hydrogenated castor oil, lecithin derivatives, polyoxyethylene sorbitol fatty acid esters, polyoxyethylene glycol fatty acid esters, polyoxyethylene castor oil, polyoxyethylene alkyl ethers, polyoxyethylene polyoxypropylene alkyl ethers, polyoxyethylene lanolin, polyoxyethylene lanolin alcohol, propylene glycol fatty acid esters and polyglycerol fatty acid esters. It is preferable tO use glycerol fatty acid esters, sorbitan fatty acid esters, polyoxyethylene hydrogenated castor oil, and propylene glycol fatty acid esters.

Examples of the fats and oils include almond oil, olive oil, sesame oil, safflower oil, soybean oil, corn oil, rape seed oil, castor oil, cotton seed oil, beef tallow and hydrogenated oils. Preferably used are soybean oil, beef tallow and hydrogenated oils.

Further, one or more aqueous solvents may be added to the composition. Examples of the aqueous solvents include ethylene glycol, propylene glycol, polyethylene glycol, glycerol and N-methyl-2-pyrrolidone. Polyethylene glycol and N-methyl-2-pyrrolidone are preferably used.

In a medicinal composition produced by adding the above-mentioned additives, the solubility of PF1022 substance or practically (substantially) water-insoluble anthelmintic analogues thereto can be elevated and thus the anthelmintic effect thereof can be enhanced. Taking usability and palatability into consideration, the composition may be absorbed by an oil absorbing carrier. Examples of the oil absorbing carrier include silica-alumina minerals, calcium carbonate, calcium phosphate, rice bran oil cake, soybean oil cake, cotton seed oil cake, corn flour, corn starch, gluten, skim milk powder and pelletized diet for livestock.

Either or both of the nonionic surfactants and fats and oils are used in an amount of 1 part by weight or above, preferably from 5 to 50 parts by weight, per part by weight of the practically water-insoluble anthelmintic compound such as PF1022 substance. When the aqueous solvent is used together, the total amount of the aqueous solvent and either or both of the nonionic surfactants and fats and oils is adjusted to 1 part by weight or above, preferably from 5 to 50 parts by weight, per part by weight of the practically water-insoluble anthelmintic compound such as PF1022 substance.

The medicinal composition of the present invention may be produced in the following manner. One or more substances selected from either or both of nonioinc surfactants and fats and oils, optionally together with one or more aqueous solvents, are mixed and heated to such a temperature as to give a solution. Next, the practically water-insoluble anthelmintic compound such as PF1022 substance is added thereto and dissolved by, for example, ultrasonication or stirring. Then, the resulting solution is allowed to cool to give the medicinal composition of the present invention.

Further, an oil absorbing carrier may be impregnated with the medicinal composition in the following manner. When the medicinal composition is in the form of a liquid, it is optionally heated to an appropriate temperature. When it is in the form of a solid, it is liquefied by heating to an appropriate temperature. Then, an oil absorbing carrier is impregnated with the liquid composition. The method for the impregnation is not particularly restricted. For example it is preferable to spray or add dropwise the liquid composition to the oil absorbing carrier while the carrier is stirred by using, for example, a stirrer or a homogenizer. PF1022 Substance may be used either as crystals or in an amorphous form.

In the medicinal composition of the present invention, the solubility of a practically water-insoluble anthelmintic compound is elevated and thus its dispersibility is improved. When the medicinal composition of the present invention is administered orally, intravenously, subcutaneously or intradermally so as to reach the digestive tract, it comes in contact with parasites in vivo at a higher frequency for a longer period, compared with the administration of such a practically water-insoluble anthelmintic compound alone, and thus the anthelmintic effect is enhanced.

The medicinal composition of the present invention can be administered to animals or humans suffered from parsitic infection orally or by injection. It may be mixed with water or feed to allow subjects to take it. The composition of the present invention can be used in an amount of 1 part by weight based on 1 to 100 part by weight of water or feed. The amount effective for treating parasitic infection varies depending on subjects, the body weight of the subjects and symptom. Typical dose to human, cattle, sheep, horse, swine, fowl, dog and cat is shown below in terms of the amount of PF1022 substance.

| Subject | Dose (mg/kg/day once or twice) | | |
| --- | --- | --- | --- |
| | Oral administration | Intravenous injection | Intramuscular injection |
| Cattle | 0.02–25 | 0.005–1 | 0.001–1 |
| Sheep | 0.02–25 | 0.005–1 | 0.001–1 |
| Horse | 0.02–2.5 | 0.005–1 | 0.001–1 |
| Swine | 0.01–2 | 0.002–1 | 0.005–1 |
| Fowl | 0.01–0.5 | 0.002–0.5 | 0.005–0.5 |
| Dog | 0.01–0.5 | 0.002–0.5 | 0.005–0.5 |
| Cat | 0.01–0.5 | 0.002–0.5 | 0.005–0.5 |
| Human | 0.02–2 | — | — |

To further illustrate the present invention, the following Examples in which PF1022 substance is employed as a practically water-insoluble anthelmintic, are given, but these Examples are not construed to limit the scope of the present invention. Unless otherwise noted, each "%" given in the Examples means % by weight. The solubility of PF1022 substance and enhancement of its efficacy in the medicinal composition of the present invention were examined in Test Examples.

TEST EXAMPLE 1

Water solubility of PF1022 substance

The compositions of Examples 1 to 9 and PF1022 substance alone, employed as a control, were tested. Each composition was weighed in a 100 ml-Erlenmeyer flask, in an amount corresponding to 50 mg of PF1022 substance and 50 ml of McDougall buffer or Clark Lubs buffer was added thereto. McDougall buffer is prepared by dissolving 7.43 g of sodium hydrogencarbonate, 7.0 g of disodium phosphate 12-hydrate, 0.34 g of sodium chloride, 0.43 g of potassium chloride, 0.10 g of magnesium chloride hexahydrate and 0.05 g of calcium chloride in 1,000 ml of water and saturating the mixture with carbon dioxide gas (pH 6.8). Clark Lubs buffer is prepared by adding 50 ml of 0.2N potassium chloride and 10.6 ml of 0.2N hydrochloric acid to 139.4 ml of water (pH 2.0). The mixture was shaken in a thermostat at 40 °±0.5° C. at a vibrational amplitude of 4 cm at 60 rpm to figure eight. Sampling was made with the lapse of time and the amount of the eluate was determined by high performance liquid chromatography. Table 1 shows the results.

TABLE 1

| | Concentration of PF1022 substance (ppm) | | | |
| --- | --- | --- | --- | --- |
| | McDougall buffer | | Clark Lubs buffer | |
| Sample | 1 hr | 24 hr | 1 hr | 24 hr |
| control | <1.0 | <1.0 | <1.0 | <1.0 |
| Example 1 | 101.6 | 17.9 | 95.8 | 17.0 |
| Example 2 | 595.0 | 52.0 | 552.7 | 55.0 |
| Example 3 | 71.1 | 226.9 | 96.3 | 217.5 |
| Example 4 | 20.2 | 101.8 | 16.7 | 93.7 |
| Example 5 | 901.9 | 910.0 | 920.4 | 908.4 |
| Example 6 | 815.0 | 859.0 | 806.7 | 779.1 |
| Example 7 | 4.0 | 11.0 | 6.8 | 11.6 |
| Example 8 | 2.0 | 9.9 | 7.4 | 10.6 |
| Example 9 | 12.0 | 6.5 | 11.2 | 5.4 |

TEST EXAMPLE 2

Solubility of PF1022 substance in serum

A 10 ml portion of PORCINE SERUM (Irvine Scientific Co.) was distributed into a tube with a stopper. One gram of the composition prepared in Example 10 was added thereto. As a control, 12.5 mg of PF1022 substance alone was used. Then, formation of precipitation was observed with the naked eye. The results are shown in Table 2.

TABLE 2

| Sample | Solubility in serum | |
|---|---|---|
| | Immediately after the treatment | 30 min. after the treatment |
| Control | Crystals of PF1022 substance was found | Crystals of PF1022 substance was found |
| Example 10 | No crystals, precipitation and turbidity was found | No crystals, precipitation and turbidity was found |

TEST EXAMPLE 3

Confirmation of enhancement of efficacy

The medicinal composition of the present invention was administered to animals in an amount corresponding to a definite amount of PF1022 substance. The whole feces was collected everyday and the number of parasitic eggs per gram of the feces (EPG) were counted. Two weeks after the initiation of the administration, each animal was dissected and the number of parasites remaining in the intestine were counted.

Table 3 shows the results of an examination on the anthelmintic effect on cattle nematodes in the digestive tract. The medicinal composition obtained in Example 1 was orally administered in a dose as corresponding to 25 mg of PF1022 substance/kg/day for two days. As a control, PF1022 substance alone was administered in the same manner as those described above. Table 4 shows the results of an examination on the anthelmintic effect on sheep nematodes in the digestive tract. Each of the medicinal composition as shown in Table 4 was orally administered in a dose corresponding to 5 mg of PF1022 substance/kg/day for two days. As a control, PF1022 substance alone was orally administered in a dose of 25 mg/kg/day for two days.

TABLE 3

| Sample | Number of eggs per gram of feces (EPG) Day after the administration of drug | | | | | | |
|---|---|---|---|---|---|---|---|
| | 0 | 1 | 3 | 5 | 7 | 10 | 14 |
| Control | 112 | 80 | 34 | 41 | 49 | 36 | 40 |
| Example 1 | 88 | 37 | 0 | 0 | 0 | 0 | 2 |

TABLE 4

| Sample | Number of eggs per gram of feces (EPG) Day after the administration of drug | | | | | | |
|---|---|---|---|---|---|---|---|
| | 0 | 1 | 3 | 5 | 7 | 10 | 14 |
| Control | 2997 | 2313 | 13 | 9 | 32 | 12 | 8 |
| Example 2 | 843 | 87 | 4 | 0 | 0 | 0 | 0 |
| Example 3 | 882 | 619 | 0 | 0 | 0 | 2 | 0 |
| Example 5 | 6255 | 5776 | 21 | 0 | 0 | 0 | 0 |

EXAMPLE 1

15 g of polyoxyethylene (20) hydrogenated castor oil, 9 g of polyethylene glycol 400 and 3 g of soybean oil were weighed into a 50 ml-beaker and heated to 60° C. Then, 3 g of PF1022 substance was slowly added thereto and dissolved by stirring with a disperser (mfd. by NITI-ON MEDICAL & PHYSICAL INSTRUMENTS CO., LTD.). The solution thus obtained was slowly added to 270 g of a standard experimental diet for cattle (mfd. by Nippon Formula Feed Co., Ltd.) contained in a V-bench blender (mfd. by Tsutsui Scientific Instruments) and homogeneously absorbed.

EXAMPLE 2

25 g of polyoxyethylene (20) hydrogenated castor oil and 25 g of polyoxyethylene (60) hydrogenated castor oil were weighed into a 100 ml-beaker and heated to 60° C. Then, 5 g of PF1022 substance was slowly added thereto and dissolved by stirring with a disperser. The mixture was slowly added to 445 g of soybean oil cake contained in a kneader ADH-J2 (mfd. by Fuji Paudal Co., Ltd.) and kneaded.

EXAMPLE 3

30 g of propylene glycol monocaprylate, 38 g of propylene glycol monostearate and 30 g of decaglyceryl monostearate were weighed into a 200 ml-beaker and heated to 50° C. Then, 2 g of PF1022 substance was slowly added thereto and mixed by stirring with a disperser. The resulting mixture was encapsulated in gelatin capsules and cooled to room temperature. After the content was solidified, the capsules were removed.

EXAMPLE 4

30 g of propylene glycol monocaprylate, 5 g of glycerol monostearate, 33 g of propylene glycol monostearate, 25 g of decaglyceryl monostearate and 5 g of decaglyceryl monomyristate were weighed into a 200 ml-beaker and dissolved by heating to 50° C. Then, 2 g of PF1022 substance was slowly added thereto and dissolved by stirring with a disperser. The resulting mixture was encapsulated in gelatin capsules and cooled to room temperature. After the content was solidified, the capsules were removed.

EXAMPLE 5

49 g of polyoxyethylene (60) hydrogenated castor oil and 48.5 g of propylene glycol monocaprylate were weighed into a 200 ml-beaker and dissolved by heating to 50° C. Then, 2.5 g of PF1022 substance was added thereto and dissolved by stirring with a disperser, followed by allowing it to stand at room temperature for cooling.

EXAMPLE 6

45 g of polyoxyethylene (60) hydrogenated castor oil, 23 g of polyoxyethylene (100) hydrogenated castor oil and 30 g of propylene glycol monocaprylate were weighed into a 200 ml-beaker and dissolved by heating to 60° C. Then, 2 g of PF1022 substance was added thereto and dissolved by stirring with a disperser. The mixture was allowed to stand at room temperature for cooling to give a semisolid product.

EXAMPLE 7

20 g of glycerol monocaprylate, 60 g of decaglyceryl monolaurate, 7.5 g of decaglyceryl tristearate and 7.5 g of decaglyceryl pentastearate were weighed into a 200 ml-beaker and dissolved by heating to 60° C. Then, 5 g of PF1022 substance was added thereto and dissolved by stirring with a disperser. The mixture was allowed to stand at room temperature for cooling to give a semisolid product.

EXAMPLE 8

47.5 g of polyoxyethylene (20) hydrogenated castor oil was introduced into a mortar and 5 g of PF1022 substance was added thereto, followed by kneading. Then, 47.5 g of polyoxyethylene (60) hydrogenated castor oil, which had been previously molten at 60° C., was slowly added thereto and kneaded to give a semi-solid product.

EXAMPLE 9

20 g of soybean oil, 12.5 g of polyoxyethylene (20) monostearate and 12.5 g of sorbitan monooleate were weighed into a 100 ml-beaker and dissolved by heating to 60° C. Then, 5 g of PF1022 substance was added thereto and dissolved by heating. The resulting mixture was slowly added to 450 g of corn flour contained in a kneader followed by kneading.

EXAMPLE 10

12.5 g of polyoxyethylene (60) hydrogenated castor oil and 12.5 g of propylene glycol monocaprylate was introduced into a 200 ml-beaker and dissolved by heating to 60° C. Separately, 50 g of N-methyl-2-pyrrolidone was weighed into a 100 ml-beaker and 1.25 g of PF1022 substance was added thereto and dissolved under stirring. These mixtures were mixed under stirring and allowed to stand at room temperature for cooling. Then, 23.75 g of water was added thereto and mixed under stirring.

While the invention has been described in detail and with reference to specific examples thereof, it will be apparent to one skilled in the art that various changes and modifications can be made therein without departing from the spirit and scope thereof.

What is claimed is:

1. A medicinal composition comprising (1) a compound represented by the following formula (I) or substantially water-insoluble anthelmintic analogues thereof as an active ingredient

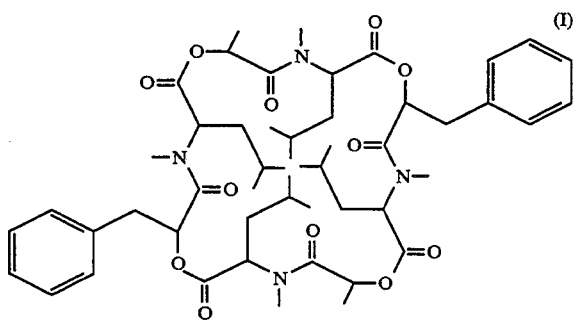

and (2) at least two nonionic surfactants, in a total amount of not less than 1 part by weight per part by weight of said compound (I).

2. A medicinal composition according to claim 1, wherein the nonionic surfactants are selected from glcyerol fatty acid esters, sorbitan fatty acid esters, polyoxyethylene sorbitan fatty acid esters, polyoxyethylene glycerol fatty acid esters, polyoxyethylene hydrogenated castor oil, lecithin derivatives, polyoxyethylene sorbitol fatty acid esters, polyoxyethylene glycol fatty acid esters, polyoxyethylene castor oil, polyoxyethylene alkyl ethers, polyoxyethylene polyoxypropylene alkyl ethers, polyoxyethylene lanolin, polyoxyethylene lanolin alcohol, propylene glycol fatty acid esters and polyglycerol fatty acid esters.

3. A medicinal composition according to claim 1, wherein the composition contains at least one compound selected from fats and oils.

4. A medicinal composition according to claim 3, wherein the fats and oils are selected from almond oil, olive oil, sesame oil, safflower oil, soybean oil, corn oil, rape seed oil, castor oil, cotton seed oil, beef tallow and hardened oils.

5. A medicinal composition according to claim 1, wherein the composition contains at least one compound selected from aqueous solvents.

6. A method of treating a parasitic infection which comprises administering to animals or humans suffering from a parasitic infection the medicinal composition according to claim 1, wherein the medicinal composition is administered orally, intravenously, subcutaneously or intradermally.

7. A medicinal composition comprising (1) a compound represented by the following formula (I) or substantially water-insoluble anthelmintic analogues thereof as an active ingredient

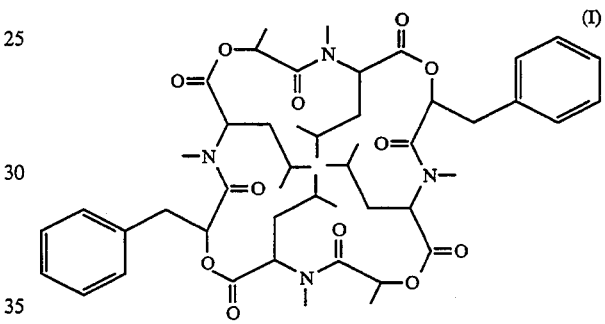

and (2) at least one nonionic surfactant, (3) one or more aqueous solvents, and (4) one or more fats and oils, wherein the total amount of the ingredients (2), (3) and (4) is at least 1 part by weight per part by weight of said compound (I).

8. A medicinal composition according to claim 7, wherein the nonionic surfactant is selected from glcyerol fatty acid esters, sorbitan fatty acid esters, polyoxyethylene sorbitan fatty acid esters, polyoxyethylene glycerol fatty acid esters, polyoxyethylene hydrogenated castor oil, lecithin derivatives, polyoxyethylene sorbitol fatty acid esters, polyoxyethylene glycol fatty acid esters, polyoxyethylene castor oil, polyoxyethylene alkyl ethers, polyoxyethylene polyoxypropylene alkyl ethers, polyoxyethylene lanolin, polyoxyethylene lanolin alcohol, propylene glycol fatty acid esters and polyglycerol fatty acid esters.

9. A medicinal composition according to claim 7, wherein the fats and oils are selected from almond oil, olive oil, sesame oil, safflower oil, soybean oil, corn oil, rape seed oil, castor oil, cotton seed oil, beef tallow and hydrogenated oils.

10. A medicinal composition according to claim 7, wherein the aqueous solvents are selected from ethylene glycol, propylene glycol, polyethylene glycol, glycerol and N-methyl-2-pyrrolidone.

11. A method of treating a parasitic infection which comprises administering to animals or humans suffering from a parasitic infection the medicinal composition according to claim 7, wherein the medicinal composition is administered orally, intravenously, subcutaneously or intradermally.

* * * * *